United States Patent
Lee

(10) Patent No.: US 10,646,401 B2
(45) Date of Patent: May 12, 2020

(54) MOXIBUSTION DEVICE

(71) Applicant: Sang Dae Lee, Suwon (KR)

(72) Inventor: Sang Dae Lee, Suwon (KR)

(\*) Notice: Subject to any disclaimer, the term of this patent is extended or adjusted under 35 U.S.C. 154(b) by 201 days.

(21) Appl. No.: 15/557,024

(22) PCT Filed: Mar. 4, 2016

(86) PCT No.: PCT/KR2016/002170
§ 371 (c)(1),
(2) Date: Sep. 8, 2017

(87) PCT Pub. No.: WO2016/144048
PCT Pub. Date: Sep. 15, 2016

(65) Prior Publication Data
US 2018/0055728 A1     Mar. 1, 2018

(30) Foreign Application Priority Data

Mar. 10, 2015 (KR) .................. 10-2015-0032935
Dec. 11, 2015 (KR) .................. 10-2015-0176758

(51) Int. Cl.
*A61H 39/06*     (2006.01)
*A61F 7/00*     (2006.01)
(Continued)

(52) U.S. Cl.
CPC .......... *A61H 39/06* (2013.01); *A61B 5/0532* (2013.01); *A61F 7/00* (2013.01); *A61F 7/007* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 6,416,534 B1* | 7/2002 | Montagnino | A61F 7/007 602/14 |
| 2013/0085556 A1* | 4/2013 | Gillespie | A61H 23/02 607/114 |
| 2016/0184173 A1* | 6/2016 | Chen | A61H 7/007 601/18 |

FOREIGN PATENT DOCUMENTS

| | | |
|---|---|---|
| KR | 10-2004-0090954 A | 10/2004 |
| KR | 10-2006-0007450 A | 1/2006 |

(Continued)

OTHER PUBLICATIONS

International Search Report for PCT/KR2016/002170 filed on Mar. 4, 2016.

*Primary Examiner* — Joseph A Stoklosa
*Assistant Examiner* — Adam J Avigan

(57) ABSTRACT

A moxibustion apparatus includes: a case; a heat storage unit arranged inside the case and including a heat storage material, a heat insulating member covering an outer surface of the heat storage material, an exposed portion exposed to the outside of the heat insulating member, a heating coil embedded in the heat storage material and electrically heated, and a charging terminal that has one side exposed to the outside of the case and is connected to an external power source to provide power to the heating coil; and a moxibustion unit configured to receive heat accumulated in the heat storage material through the exposed portion to locally heat acupuncture points of a user's abdomen, and including a protrusion portion that protrudes to have an end portion thereof formed into a spherical shape or a gently curved shape and is exposed to the outside of the case.

9 Claims, 13 Drawing Sheets

(51) Int. Cl.
*A61H 39/04* (2006.01)
*A61B 5/053* (2006.01)
*A61H 39/00* (2006.01)
A61B 18/12 (2006.01)
A61H 9/00 (2006.01)

(52) U.S. Cl.
CPC ........... *A61H 39/002* (2013.01); *A61H 39/04* (2013.01); *A61B 18/12* (2013.01); *A61F 2007/0018* (2013.01); *A61F 2007/0022* (2013.01); *A61F 2007/0071* (2013.01); *A61F 2007/0087* (2013.01); *A61H 9/0057* (2013.01); *A61H 2201/02* (2013.01); *A61H 2201/0228* (2013.01); *A61H 2201/0257* (2013.01); *A61H 2201/165* (2013.01); *A61H 2201/5023* (2013.01); *A61H 2201/5043* (2013.01); *A61H 2201/5082* (2013.01)

(56) References Cited

FOREIGN PATENT DOCUMENTS

| KR | 10-2007-0068059 A | 6/2007 |
| KR | 20-2009-0000554 U | 1/2009 |
| KR | 10-2013-0130417 A | 12/2013 |
| KR | 10-2014-0088478 A | 7/2014 |

\* cited by examiner

MOXIBUSTION DEVICE

CROSS REFERENCE PARAGRAPH

This application is a U.S. National Stage of PCT/KR2016/002170, filed Mar. 4, 2016, which claims the priority benefit of Korean Patent Application Nos. 10-2015-0032935, filed on Mar. 10, 2015 and 10-2015-0176758 filed on Dec. 11, 2015, in the Korean Intellectual Property Office, the disclosures of which are incorporated herein by reference.

BACKGROUND OF THE INVENTION

1. Field of the Invention

The present invention relates to a moxibustion apparatus and, more particularly, to a moxibustion apparatus for locally heating acupuncture points or the like.

2. Description of the Prior Art

Generally, thermotherapy is known to be one of the most widely used physiotherapy methods for treating nervous and muscular fatigue by improving blood circulation or metabolism through heat. Particularly, the thermotherapy on the abdomen is known to be effective in the prevention and treatment of various diseases by heating the internal organs, and various devices such as a fomentation apparatus, a cauterizer (moxibustion apparatus), and the like have been developed as devices for heating the abdomen.

As a typical warming device, a fomentation apparatus heats the abdomen using a wide surface area of the apparatus itself in a method of widely applying heat over the entire abdomen. Such a method of widely applying the heat over the abdomen surface has an effect of temporarily heating the abdomen surface and the subcutaneous tissues, but it is difficult to expect an effect of heating even the deep region of the abdomen. That is, since the autonomic nervous system in which a temperature inside the human body tends to be lowered to keep the balance when a temperature outside a human body is raised acts in the human body, a temperature inside the abdomen may be lowered when heat is applied to the surface of the abdomen through the fomentation apparatus, and the inside of the abdomen may get rather cold due to the fomentation apparatus, which may result in deteriorating the function of the internal organs.

Therefore, a moxa treatment method is more effective as a method of heating the deep region or the internal organs in the abdomen. Moxibustion is one of the typical oriental medicine treatments that contribute to the prevention and treatment of various diseases by burning medicinal substances such as mugwort on the body surface and causing local heat stimulation to the living body. Such a moxibustion is known to be effective in treating or preventing diseases of the internal organs by heating the inside of the abdomen. However, since the medicinal substances must be burned on the body surface, there are many inconveniences in the procedure such as generation and treatment of ashes, smell due to combustion, restriction of place and time, and the like. In order to solve these problems, various kinds of cauterizers or moxibustion apparatuses have been developed, but there is a limitation that the medicinal substances must still be burned. Therefore, the cauterizers or moxibustion apparatuses still have a conventional problem that they are inconvenient for regular use in everyday life.

SUMMARY OF THE INVENTION

The present invention has been made in order to solve the above-mentioned problems in the prior art and an aspect of the present invention is to provide a moxibustion apparatus which may be easily carried and used and may be convenient for regular use in everyday life or even during outside activities.

In accordance with an aspect of the present invention, there is provided a moxibustion apparatus including: a case; a heat storage unit configured to be arranged inside the case and to include a heat storage material, a heat insulating member that covers an outer surface of the heat storage material, an exposed portion that is exposed to the outside of the heat insulating member, a heating coil that is embedded in the heat storage material and electrically heated, and a charging terminal that has one side exposed to the outside of the case and is connected to an external power source to provide power to the heating coil; and a moxibustion unit configured to receive heat accumulated in the heat storage material through the exposed portion to locally heat acupuncture points of a user's abdomen, and to include a protrusion portion that protrudes to have an end portion thereof formed into a spherical shape or a gently curved shape and is exposed to the outside of the case.

In accordance with another aspect of the present invention, there is provided a moxibustion apparatus including: a case configured to include a front case, a rear case, and an inner case, wherein the inner case includes a heat radiation port; a heat storage unit configured to be arranged inside the case and to include a heat storage material, a heat insulating member that covers an outer surface of the heat storage material, and an exposed portion that is exposed to the outside of the heat insulating member and is arranged to correspond to the heat radiation port; a moxibustion unit configured to receive heat accumulated in the heat storage material through the exposed portion to locally heat acupuncture points of a user's abdomen, and to have one side thereof exposed to the outside of the case; and a heat radiation amount adjusting unit configured to be arranged between the exposed portion and the moxibustion unit to adjust an amount of heat radiation through the heat radiation port.

In accordance with still another aspect of the present invention, there is provided a moxibustion apparatus including: a case; a heat storage unit configured to be provided inside the case to accumulate heat by power supplied from the outside, and to radiate the accumulated heat through a heat radiation port; a moxibustion unit configured to receive the heat radiated from the heat storage unit to heat a human body; and a heat insulating unit configured to block or allow transfer of the heat provided from the heat storage unit.

As described above, the moxibustion apparatus according to the embodiments of the present invention may perform moxibustion on acupuncture points or Zhongwan points of the abdomen by heating a heat storage unit through an external power source for a predetermined time period and then radiating the heat accumulated in the heat storage unit through a moxibustion unit.

In addition, the moxibustion apparatus according to the embodiments of the present invention may be very easily carried and convenient for regular use even during outdoor activities and everyday life by performing a moxibustion function through the accumulated heat after a certain time period of charge (heat storage). This can be contrasted with the inconvenience of moxibustion in everyday life and outdoor activities because a conventional moxibustion technique locally heats acupuncture points or the like by burning medicinal substances.

In addition, the moxibustion apparatus according to the embodiments of the present invention may be used for locally heating the acupuncture points or Zhongwan points of the abdomen. Here, a heat storage material is entirely surrounded by a heat insulating member to minimize unnecessary heat radiation, and heat transfer and heat radiation is achieved only through an exposed portion. Therefore, the usage time of the moxibustion apparatus according to the embodiments of the present invention can be greatly increased as compared with the conventional moxibustion apparatus in which heat is radiated through the entire outer surface thereof. In addition, since heat radiation is performed in a state in which the protruding moxibustion unit is embedded in the abdomen portion by a predetermined amount due to the pressing of a belt or the like, sufficient heat radiation is possible even in a minimum amount of heat radiation.

In addition, the moxibustion apparatus according to the embodiments of the present invention may intensively and locally heat the acupuncture points or Zhongwan points of the abdomen, so that it is possible to obtain an effect of heating the deep region and the internal organs in the abdomen unlike the conventional moxibustion apparatus. Thus, it can be expected to improve the function of major organs in the abdomen such as the stomach, lung, liver, spleen, kidney, etc. In addition, the whole circulatory system of the human body is improved and the circulation of the blood is smooth so that the vitality and health of the human body are improved.

In addition, the moxibustion apparatus according to the embodiments of the present invention can be easily worn by a belt or the like, so that it can be continuously used even when a user is engaged in external activities or everyday life. In addition, the moxibustion apparatus according to the embodiments of the present invention is rechargeable, so that there is no fear of being affected by electromagnetic waves even when it is used for a long time period. In addition, in the conventional moxibustion method, smell, ashes, and the like are generated, whereas the moxibustion apparatus according to the embodiments of the present invention generates no smell, ashes, etc., due to a heat storage method.

In addition, in the moxibustion apparatus according to the embodiments of the present invention, the temperature thereof can be easily adjusted through a heat radiation amount adjusting unit, so that it is possible to adjust an amount of heat radiation according to each user's desired temperature while preventing burns due to heat radiation. In addition, the moxibustion apparatus according to the embodiments of the present invention may be made smaller in size and weight in comparison with the conventional general moxibustion apparatus or the like, so that the moxibustion apparatus cannot be exposed to the outside by being worn in outerwear, and can be usefully utilized in outdoor activities in winter and in everyday life.

In addition, in the moxibustion apparatus according to the embodiments of the present invention, a heat storage unit in which heat is accumulated and a moxibustion unit that heats a human body can be separately formed so that a heat storage material can be made of a relatively inexpensive material, and the moxibustion unit having the a relatively small volume can be made of expensive materials that have various beneficial effects such as anion and far-infrared emission, and the like. Therefore, it is possible to use a heat storage material formed of an inexpensive material while enjoying various beneficial effects due to expensive materials, thereby minimizing an increase in manufacturing cost.

BRIEF DESCRIPTION OF THE DRAWINGS

The above and other aspects, features and advantages of the present invention will be more apparent from the following detailed description taken in conjunction with the accompanying drawings, in which.

DETAILED DESCRIPTION OF THE EXEMPLARY EMBODIMENTS

Hereinafter, embodiments of the present invention will be described in detail with reference to the accompanying drawings. However, it is to be understood that the following embodiments are provided to facilitate understanding of the present invention, and the scope of the present invention is not limited to the following embodiments. When it is determined that a detailed description of a known art related to the present invention may unnecessarily obscure the gist of the present invention while describing the present invention, the detailed description thereof will be omitted.

Figure 1A:
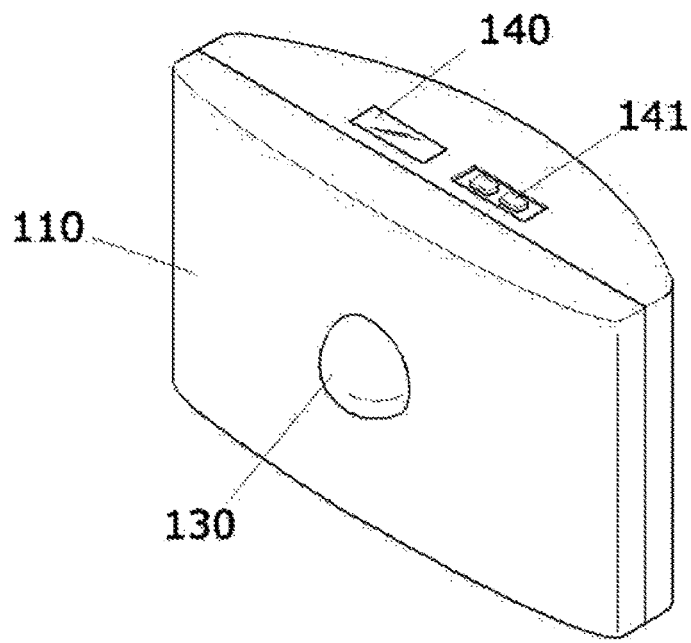
FIGS. 1A and 1B are conceptual views showing a moxibustion apparatus according to a first embodiment of the present invention.
Figure 1B:
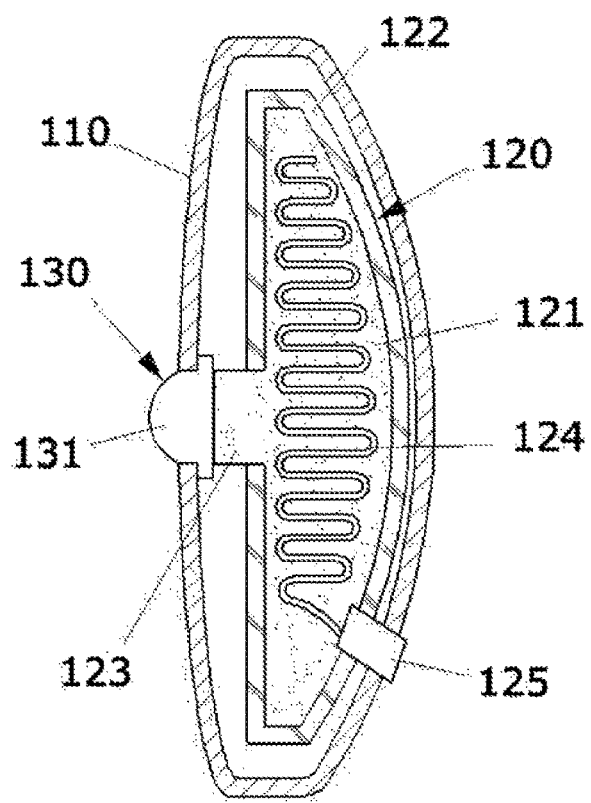

FIGS. 1A and 1B are conceptual views showing a moxibustion apparatus according to a first embodiment of the present invention.

It is noted that FIG. 1A schematically shows the outer appearance of a moxibustion apparatus 100, and FIG. 1B schematically shows the inside of the moxibustion apparatus 100.

Referring to FIGS. 1A and 1B, the moxibustion apparatus 100 according to the present embodiment may include a case 110, a heat storage unit 120 installed inside the case 110, and a moxibustion unit 130 having one side exposed to the outside of the case 110. Such a moxibustion apparatus 100 can be worn on a user's waist using a belt or the like, and the exposed moxibustion unit 130 is brought into close contact with acupuncture points of the abdomen to locally heat the acupuncture points, thereby obtaining a moxibustion effect.

In particular, the moxibustion apparatus 100 according to the present embodiment can be effectively used for performing moxibustion on Zhongwan points at the upper end of the abdomen. The Zhongwan points are acupuncture points positioned midway stomach between the navel and the solar plexus, and are also called Taicang points. It is known that the moxibustion on Zhongwan points is effective in increasing the temperature inside the abdomen to prevent medical diseases of the gastrointestinal tract, large and small intestines, and circulatory system and to increase immunity. However, there is a problem in that the moxibustion on Zhongwan points is difficult to be performed in everyday life because of their positions and characteristics of a conventional general moxibustion technique (a method of burning medicinal substances such as mugwort in the acupuncture points to locally heat the acupuncture points). The moxibustion apparatus 100 according to the present embodiment can locally heat the acupuncture points through the moxibustion unit 130 in a heat accumulating manner and can be worn using a belt or the like so that it is not difficult to use the moxibustion apparatus 100 in everyday life.

Hereinafter, each component of the above-described moxibustion apparatus 100 will be described in more detail.

Referring to FIG. 1, the moxibustion apparatus 100 according to the present embodiment may include the case 110. The case 110 may form a mounting space in which the heat storage unit 120, and the like may be arranged.

In addition, the moxibustion apparatus 100 according to the present embodiment may include the heat storage unit 120 arranged inside the case 110. The heat storage unit 120 may include a heat storage material 121 and may accumulate heat required for moxibustion. The heat storage material 121 may include various materials capable of storing heat. For example, the heat storage material 121 may include one or more materials of stone, ocher stone, kaolin, elvan, cast iron, and ceramic.

The heat storage unit 120 may include a heat insulating member 122. The heat insulating member 122 entirely covers an outer surface of the heat storage material 121 excluding an exposed portion 123 so that the heat accumulated in the heat storage material 121 is radiated through the exposed portion 123. Such a heat insulating member 122 covers the outer surface of the heat storage material 121 to improve the heat storage performance of the heat storage material 121 and minimize unnecessary heat radiation in portions other than the exposed portion 123, thereby increasing a usage time of the moxibustion apparatus 100.

The heat storage unit 120 may include the exposed portion 123. The exposed portion 123 may protrude from the heat storage material 121 and be exposed to the outside of the heat insulating member 122. Alternatively, the exposed portion 123 may refer to one side of the heat storage material 121 exposed to the outside of the heat insulating member 122. The exposed portion 123 may transfer the heat accumulated in the heat storage material 121 to the moxibustion unit 130, which will be described later. For example, the exposed portion 123 may be brought into contact with the moxibustion portion 130 to transfer the accumulated heat to the moxibustion portion 130. In this embodiment, a case in which the exposed portion 123 is in contact with the moxibustion unit 130 is shown. Alternatively, the exposed portion 123 may be arranged adjacent to the moxibustion unit 130 with a predetermined gap therebetween to transfer the accumulated heat to the moxibustion unit 130. Further, the exposed portion 123 may be indirectly brought into contact with the moxibustion portion 130 to transfer the accumulated heat to the moxibustion portion 130. Here, the "indirect contact" refers to a case in which heat is transferred between the exposed portion 123 and the moxibustion unit 130 with another heat transfer means interposed therebetween.

The heat storage unit 120 may include a heating coil 124 and a charging terminal 125. The heating coil 124 may be embedded in the heat storage material 121 and may be electrically heated to accumulate heat in the heat storage material 121. The charging terminal 125 may provide power necessary for generating heat to the heating coil 124, and at least a part of the charging terminal 125 may be exposed to the outside of the case 110 and connected to an external power source. For example, the charging terminal 125 may be connected to the external power source through a charging cable or a separate charging device, and thereby may receive power.

Meanwhile, the moxibustion apparatus 100 according to the present embodiment may include the moxibustion unit 130. The moxibustion unit 130 may transfer the accumulated heat to acupuncture points or Zhongwan points of the abdomen. One side of the moxibustion unit 130 may be arranged inside the case 110 and may be directly or indirectly brought into contact with the exposed portion 123, thereby receiving the heat accumulated in the heat storage material 121.

A protrusion portion 131 exposed to the outside of the case 110 may be provided on the other side of the moxibustion unit 130. The protrusion portion 131 may be brought into close contact with the acupuncture points or the Zhongwan points of the abdomen to locally heat the acupuncture points or the Zhongwan points. The protrusion portion 131 may protrude toward the outside of the case 110 or toward the abdomen of a user to a predetermined degree. Further, a protruding end portion of the protrusion portion 131 may be formed into a spherical shape or a gently curved shape. Such a protrusion portion 131 may press the acupuncture points or the Zhongwan points to a predetermined degree by fastening a belt portion when the moxibustion apparatus 100 is worn. Therefore, it is possible to obtain an acupressure effect of the acupuncture points in parallel with a moxibustion function through the local heat. In addition, since the end portion formed into the spherical or gently curved shape is embedded in the abdomen or the Zhongwan points to a certain degree due to a pressing force, unnecessary external heat radiation may be minimized and a heat transfer surface area may be increased, so that a sufficient thermal effect can be expected.

The moxibustion unit 130 may include one or more materials of jade, germanium, new stone, marble, gold, and silver. However, the moxibustion unit 130 may be any material as long as it can transfer heat to the acupuncture points and the like, and is not limited to the above-described materials.

If necessary, the moxibustion apparatus 100 according to the present embodiment may include a temperature display window 140. The temperature display window 140 may be provided on an outer surface of the case 110, and may display a temperature of at least one of the heat storage material 121 and the moxibustion unit 130 through a temperature sensor (not shown) provided in the at least one of the heat storage material 121 and the moxibustion unit 130. In addition, if necessary, a switch unit 141 for on/off operation of a user, temperature control, and the like may be provided on the outer surface of the case 110.

Figure 2A:
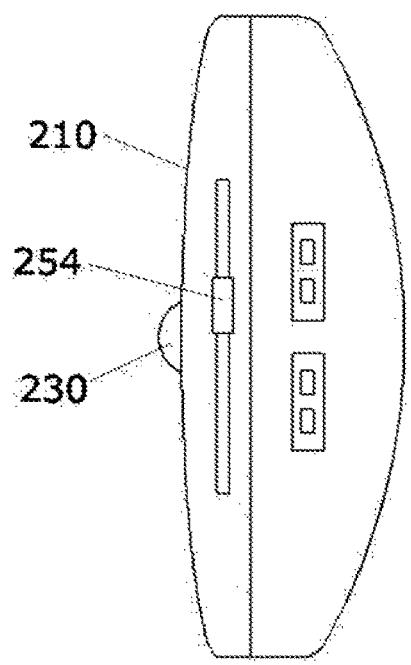
FIGS. 2A and 2B are conceptual views showing a moxibustion apparatus according to a second embodiment of the present invention.
Figure 2B:
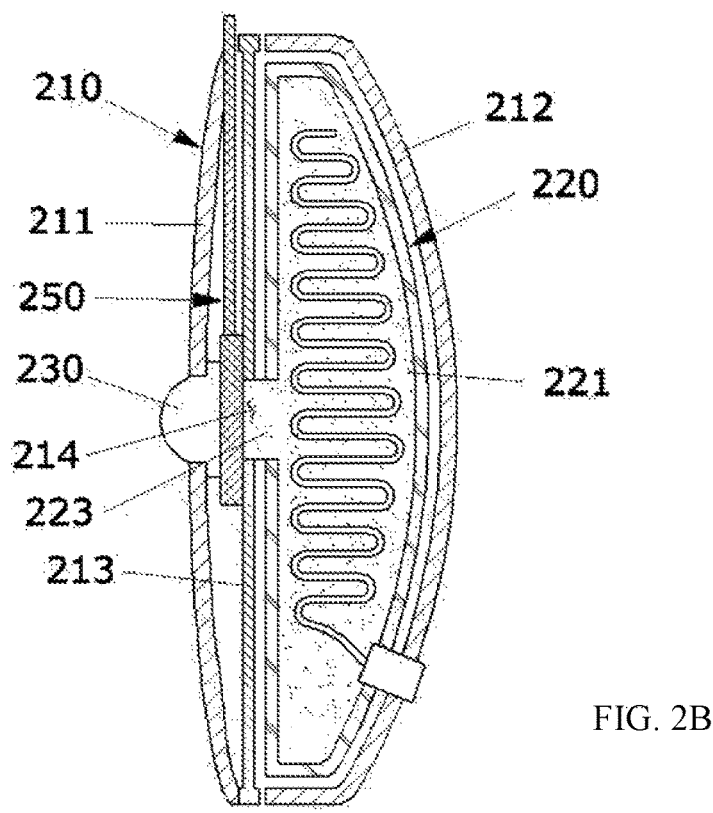

FIGS. 2A and 2B are conceptual views showing a moxibustion apparatus according to a second embodiment of the present invention.

It is noted that FIG. 2A schematically shows the outer appearance of a moxibustion apparatus 200 viewed from above, and FIG. 2B schematically shows the inside of the moxibustion apparatus 200.

Referring to FIGS. 2A and 2B, the moxibustion apparatus 200 according to the present embodiment may include a case 210. The case 210 may form an overall appearance of the moxibustion apparatus 200 and may form a mounting space in which a heat storage unit 220 and the like are arranged. This is similar to the case 110 of the above-described moxibustion apparatus 100.

In addition, the case 210 according to the present embodiment may include a front case 211, a rear case 212 and an inner case 213. The front case 211 and the rear case 212 may form the outer surface of the moxibustion apparatus 200, and the inner case 213 may be arranged in the mounting space of the case 210. In addition, the inner case 213 may be arranged between the heat storage unit 220 and a moxibustion unit 230. In this case, a heat radiation port 214 may be provided in the inner case 213 so that an exposed portion 223 of a heat storage material 221 can approach or transfer heat to the moxibustion unit 230.

Meanwhile, the moxibustion apparatus 200 according to the present embodiment may include the heat storage unit 220 and the moxibustion unit 230. The heat storage unit 220 is used for accumulating heat required for moxibustion through an external power source, and may be formed similarly to the heat storage unit 120 of the above-described embodiment. The moxibustion unit 230 is used for locally heating acupuncture points or Zhongwan points of the abdomen through accumulated heat, and may be formed similarly to the moxibustion unit 130 of the above-described embodiment. However, in the case of the moxibustion apparatus 200 according to the present embodiment, a heat radiation amount adjusting unit 250 may be arranged between the exposed portion 223 and the moxibustion unit 230, and for this, a predetermined gap may be provided between the exposed portion 223 and the moxibustion unit 230.

In addition, the moxibustion apparatus 200 according to the present embodiment may include the heat radiation amount adjusting unit 250. The heat radiation amount adjusting unit 250 intervenes between the exposed portion 223 and the moxibustion unit 230 to adjust the heat transfer from the exposed portion 223 to the moxibustion unit 230. It is noted that FIGS. 2A and 2B schematically show only the arrangement of the heat radiation amount adjusting unit 250 for the sake of convenience.

Figure 3:
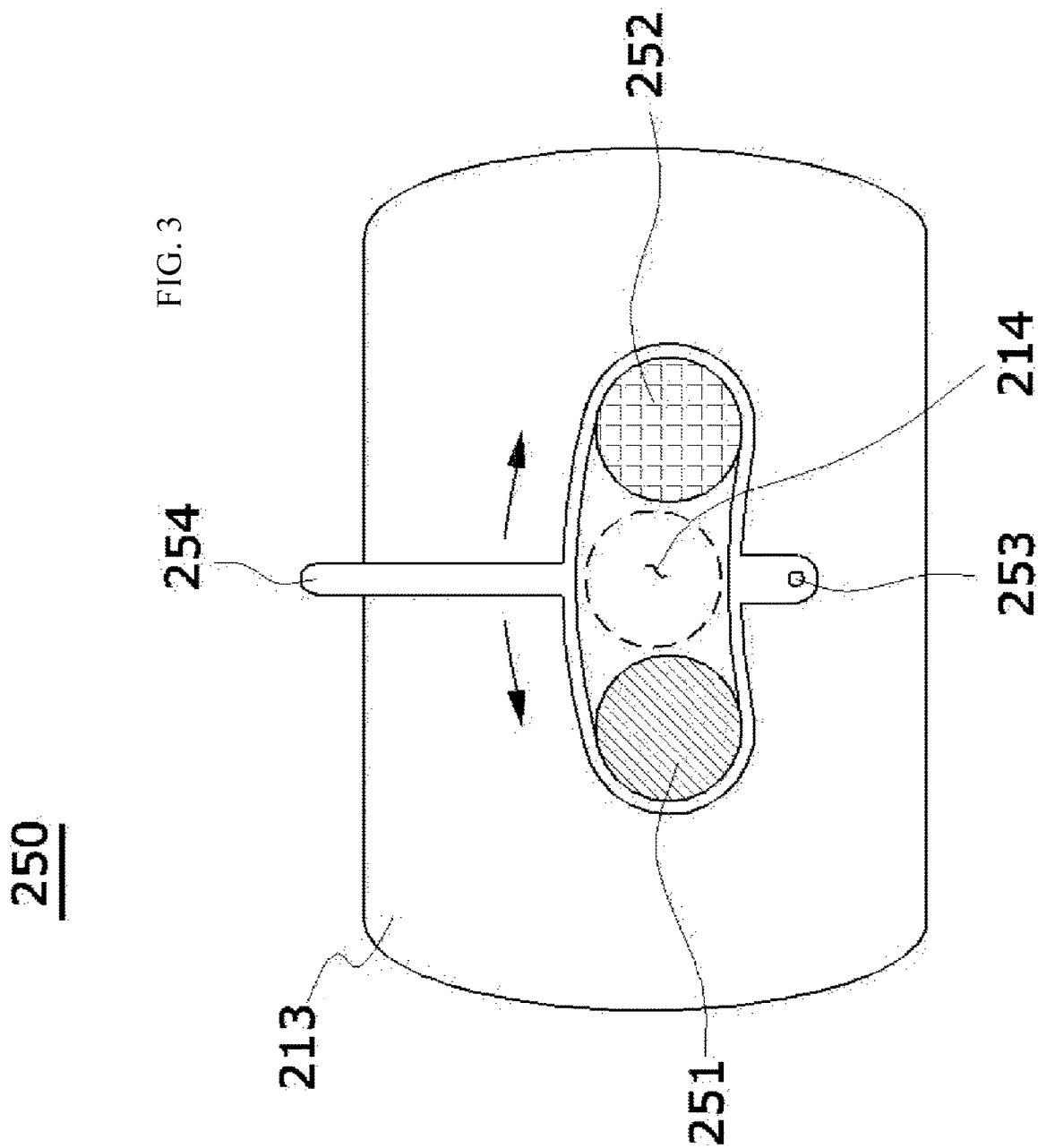
FIG. 3 is a schematic view showing a first embodiment of a heat radiation amount adjusting unit shown in FIGS. 2A and 2B.

FIG. 3 is a schematic view showing a first embodiment of a heat radiation amount adjusting unit shown in FIGS. 2A and 2B.

Referring to FIG. 3, the heat radiation amount adjusting unit 250 may include a heat insulating block 251 and a heat transfer block 252. The heat insulating block 251 may have lower thermal conductivity than the heat transfer block 252, and the heat transfer block 252 may be formed to have higher thermal conductivity. For example, the heat transfer block 252 may include at least one of copper, brass, a copper-nickel alloy, and a copper-silver alloy.

The heat insulating block 251 and the heat transfer block 252 may be spaced apart from each other by a predetermined distance with respect to the heat radiation port 214 of the inner case 213.

More preferably, the heat insulating block 251 and the heat transfer block 252 may be spaced apart from each other by a predetermined distance larger than the size of the heat radiation port 214. This is to further facilitate the temperature adjustment of the moxibustion unit 230 through the heat radiation amount adjusting unit 250 by establishing each of a state in which the heat insulating block 251 is arranged to correspond to the heat ration port 214, a state in which the heat radiation port 214 is arranged between the heat insulating block 251 and the heat transfer block 252, and a state in which the heat transfer block 252 is arranged to correspond to the heat radiation port 214.

Meanwhile, the heat radiation amount adjusting unit 250 may be formed to be movable relative to the heat radiation port 214. More specifically, one side of the heat radiation amount adjusting unit 250 may be coupled to the inner case 213 by a hinge 253, and may be rotated about the hinge 253 by a predetermined degree. Thus, the heat insulating block 251 and the heat transfer block 252 may be moved relative to the heat radiation port 214. In other words, as the heat radiation amount adjusting unit 250 is rotated about the hinge 253, the heat insulating block 251 and the heat transfer block 252 may be arranged in at least one state of a state in which the heat insulating block 251 is arranged to correspond to the heat radiation port 214 (hereinafter, referred to as "heat insulation state"), a state in which the heat radiation port 214 is arranged between the heat insulating block 251 and the heat transfer block 252 (hereinafter, referred to as "gap state"), and a state in which the heat transfer block 252 is arranged to correspond to the heat radiation port 214 (hereinafter, referred to as "heat transfer state").

In the heat insulation state in which the heat insulating block 251 is arranged to correspond to the heat radiation port 214, heat transfer from the exposed portion 223 to the moxibustion unit 230 may be blocked to a predetermined degree by the heat insulating block 251 (see FIG. 2B). That is, an amount of heat radiation from the exposed portion 223 to the moxibustion unit 230 may be reduced and the temperature of the moxibustion unit 230 may be lowered to a predetermined degree. In the heat transfer state in which the heat transfer block 252 is arranged to correspond to the heat radiation port 214, the heat of the exposed portion 223 may be transferred to the moxibustion unit 230 via the heat transfer block 252. Since the heat transfer block 252 has higher thermal conductivity than the heat insulating block 251, the amount of heat radiation to the moxibustion unit 230 may be increased and the temperature of the moxibustion unit 230 may be increased to a predetermined degree as compared with the heat insulation state. On the other hand, in the gap state in which the heat radiation port 214 is arranged between the heat insulating block 251 and the heat transfer block 252, an amount of heat radiation may be adjusted to an intermediate level between the heat insulation state and the heat transfer state.

Meanwhile, the heat radiation amount adjusting unit 250 may include a lever portion 254 that is provided on the other side of a coupled portion by the hinge 253 and exposed to the outside of the case 210 (see FIG. 2A). The lever portion 254 is exposed to the outside of the case 210 so that a user can move the heat radiation amount adjusting unit 250 as needed. That is, the user can rotate the heat radiation amount adjusting unit 250 to a predetermined degree through the lever portion. As the heat radiation amount adjusting unit 250 is rotated, state-switching may be performed between the heat insulation state, the heat transfer state, and the gap state. Accordingly, the user can appropriately adjust the temperature of the moxibustion unit 230 according to the usage, taste, and the like when using the moxibustion apparatus 200.

Figure 4:
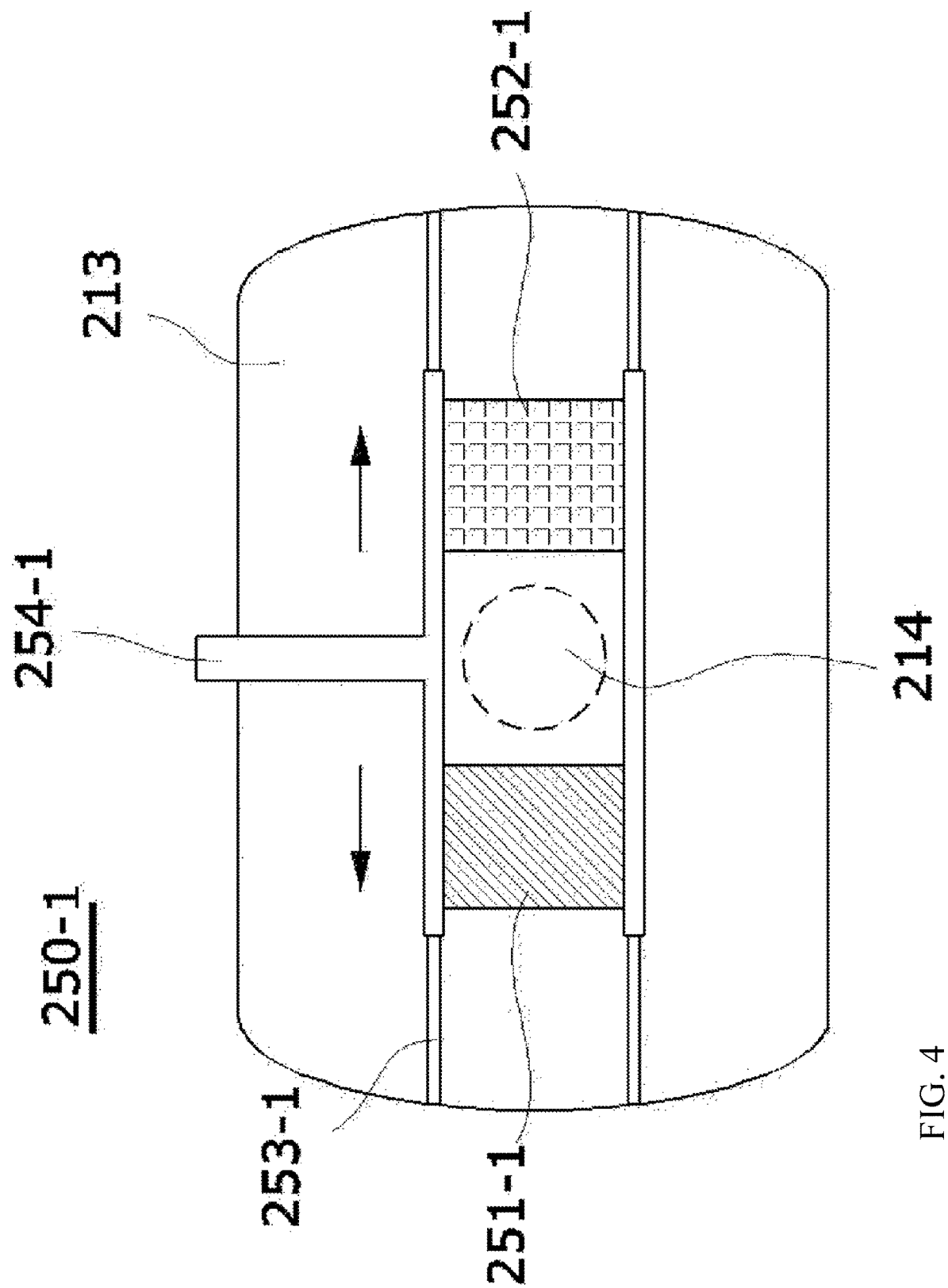
FIG. 4 is a schematic view showing a second embodiment of a heat radiation amount adjusting unit shown in FIGS. 2A and 2B.

FIG. 4 is a schematic view showing a second embodiment of a heat radiation amount adjusting unit shown in FIGS. 2A and 2B.

Referring to FIG. 4, a heat radiation amount adjusting unit 250-1 may include a heat insulating block 251-1, a heat transfer block 252-1, and a lever portion 254-1. These may be formed in a similar manner to that in the heat insulating block 251, the heat transfer block 252, and the lever portion 254 of the above-described embodiment.

However, the heat radiation amount adjusting unit 250-1 according to the present embodiment may be mounted on the inner case 213 through guide rails 253-1 and may be moved along the guide rails 253-1 by a predetermined distance. That is, the heat radiation amount adjusting unit 250-1 according to the present embodiment is moved laterally along the guide rails 253-1 so that state-switching may be performed between the heat insulation state, the heat transfer state, and the gap state.

Figure 5:
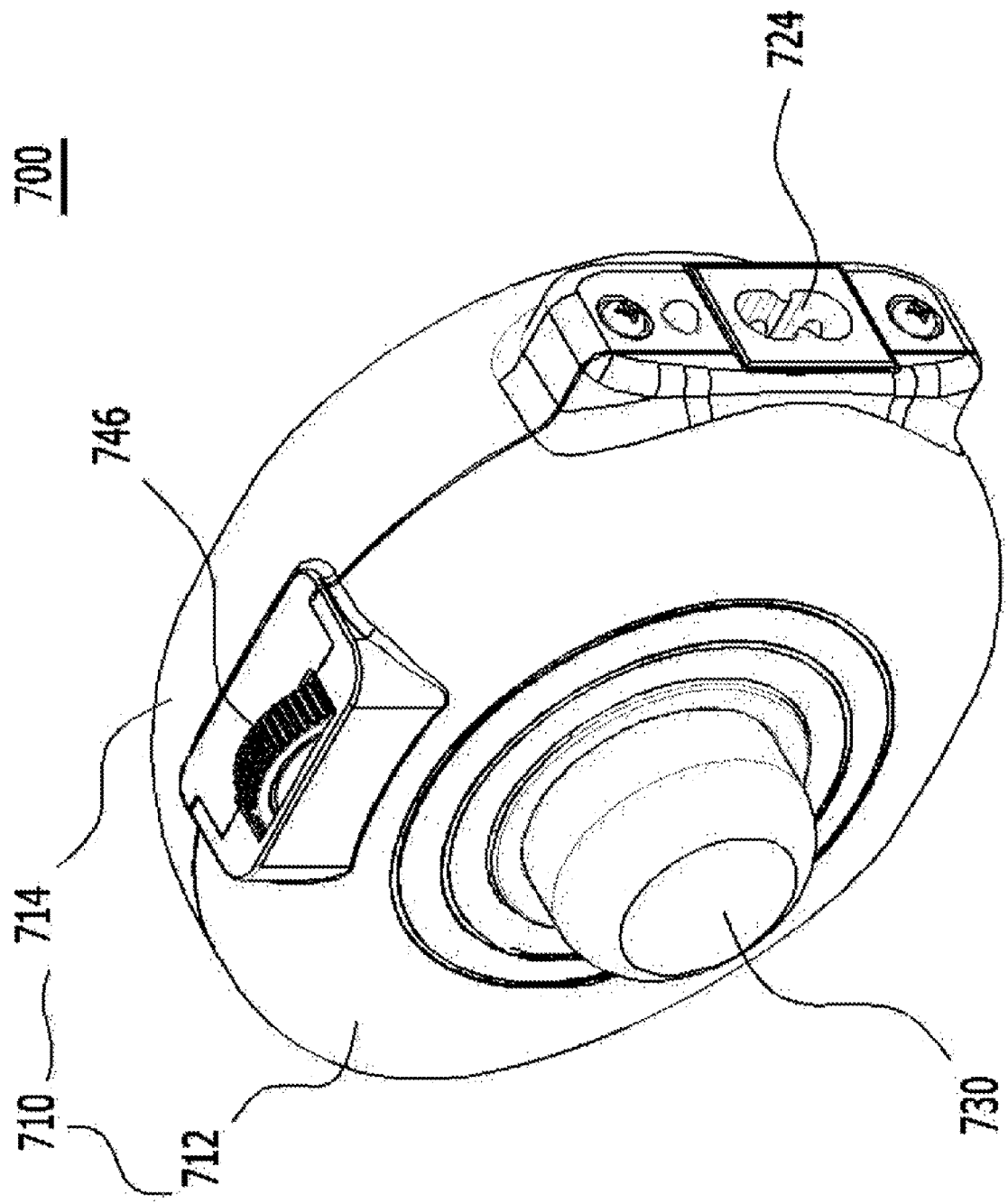
FIG. 5 is a view showing a moxibustion apparatus according to a third embodiment of the present invention.
Figure 6:
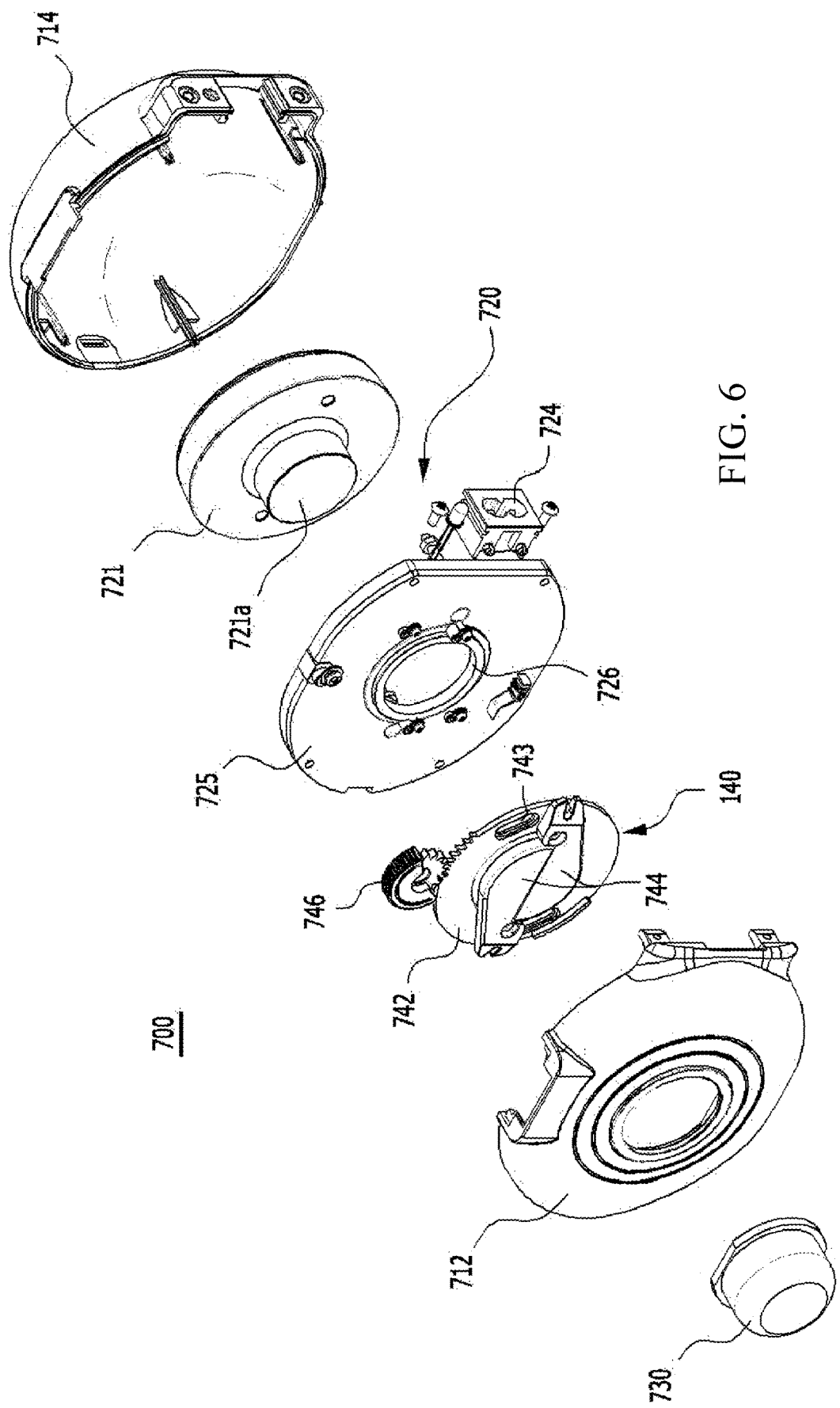
FIG. 6 is an exploded perspective view showing the moxibustion apparatus shown in FIG. 5.
Figure 7:
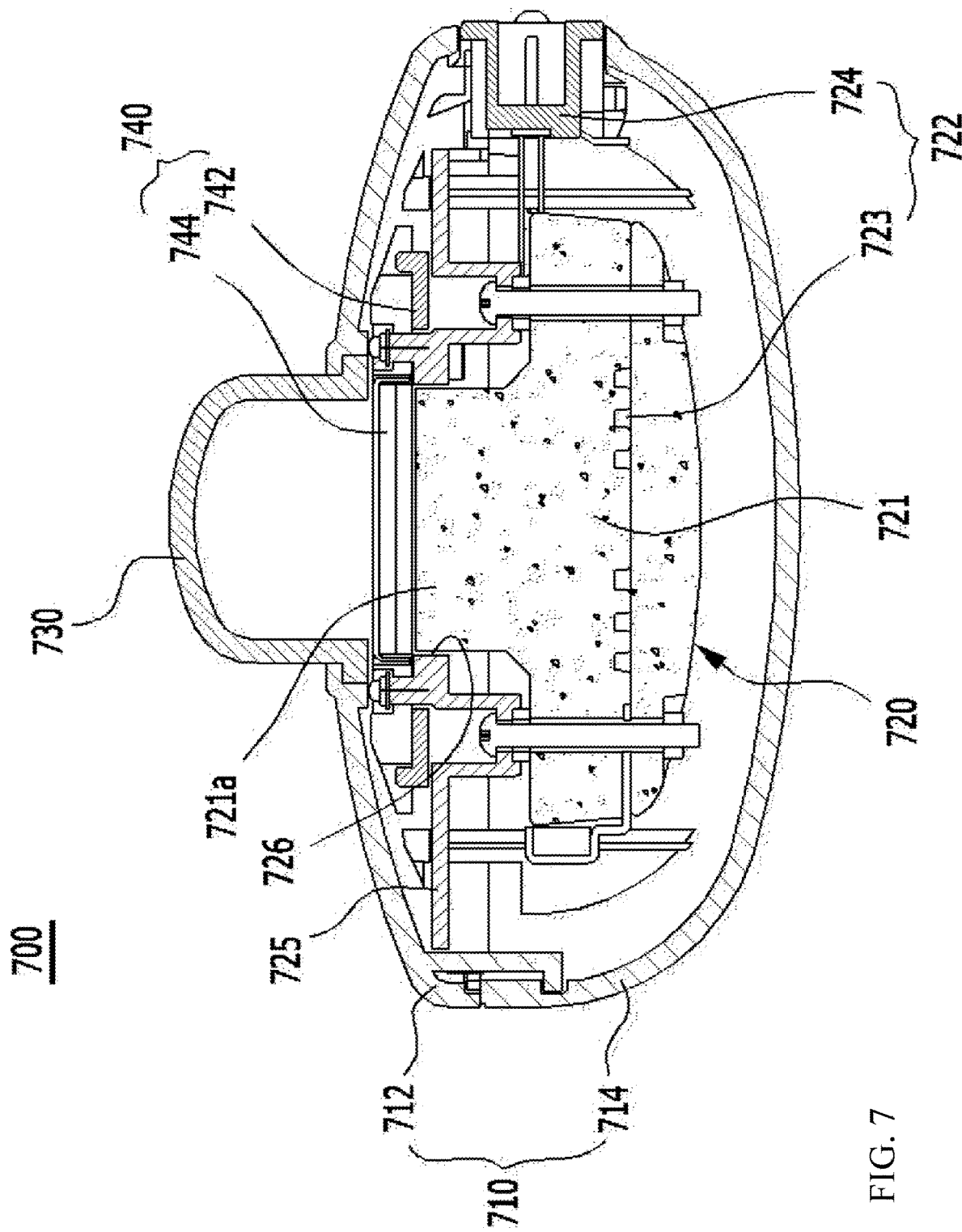
FIG. 7 is a schematic cross-sectional view showing the moxibustion apparatus shown in FIG. 5.
Figure 8:
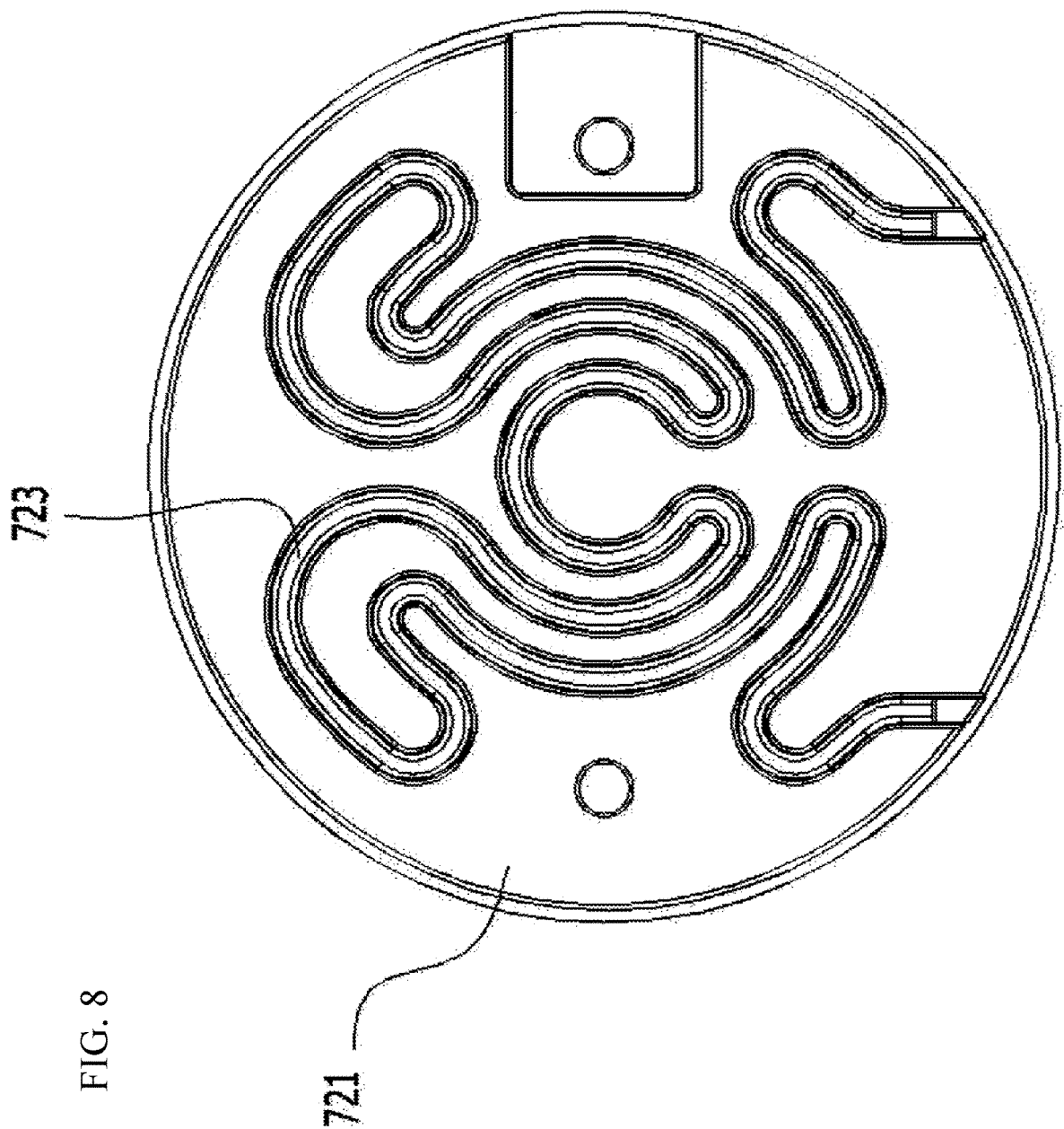
FIG. 8 is a diagram schematically showing a state in which a heating coil is embedded in a heat storage material in the moxibustion apparatus shown in FIG. 5.

FIG. 5 is a view showing a moxibustion apparatus according to a third embodiment of the present invention, FIG. 6 is an exploded perspective view showing the moxibustion apparatus shown in FIG. 5, and FIG. 7 is a schematic cross-sectional view showing the moxibustion apparatus shown in FIG. 5.

Referring to FIGS. 5 to 7, a moxibustion apparatus 700 according to the present embodiment may include a case 710, a heat storage unit 720 that is installed inside the case 710 to generate heat, a moxibustion unit 730 that receives the heat provided from the heat storage unit 720 to heat a human body, and a heat insulating unit 740 that can block or allow transfer of the heat provided from the heat storage unit 720.

Specifically, the case 710 has a receiving space therein. The case 710 may be divided into an upper case 712 and a lower case 714, and the heat storage unit 720 and the like may be installed in the receiving space formed in the case 710.

The heat storage unit 720 is arranged in the receiving space of the case 710 and includes a heat storage material 721 that can accumulate heat required for moxibustion, a heating member 722 that can be embedded in the heat storage material 721 and can be electrically heated to accumulate heat in the heat storage material 721, and a partition member 725 that can restrict the heat radiated to the heat storage material 721 from being directed to the moxibustion unit 730 to be described later.

The heat storage material 721 is arranged in the receiving space of the case 710 and is capable of accumulating heat required for moxibustion through an external power source. The heat storage material 721 is formed of a material capable of accumulating heat, and a protrusion member 721a protrudes on one side of the heat storage material 721 so that the accumulated heat can be effectively transferred to the moxibustion unit 730.

At this time, the heat storage material 721 may be formed of various materials capable of storing heat. That is, the heat storage material 721 is not limited as long as it is a material capable of accumulating heat by a heating member 722 to be described later. For example, the heat storage material 721 may be formed of various materials such as stone, jade, ceramic, ocher stone, kaolin, elvan, germanium, ceramic, water, iron, and the like.

The heating member 722 may be electrically heated to accumulate heat in the heat storage material 721, and may be constituted of a heating coil 723 and a charging terminal 724. That is, as shown in FIG. 7, the heating coil 723 may be embedded to be evenly distributed over the entire surface of the heat storage material 721 so that heat can be accumulated in the heat storage material 721 through electric heating. In addition, the charging terminal 724 may provide power necessary for generating heat to the heating coil 723, and at least a part of the charging terminal 724 may be exposed to the outside of the case 710 to be connected to an external power source. For example, the charging terminal 724 may be connected to the external power source through a charging cable or a separate charging device, and thereby may receive power.

The heating coil can be substituted by a conventional heating device such as a Positive Temperature Coefficient (PTC) heater or a sheath heater.

The partition member 725 divides the receiving space in the case 710 to restrict the heat accumulated in the heat storage material 721 from being directed to the moxibustion unit 730. Here, a heat radiation port 726 may be formed in a portion of the partition member 725 so as to allow heat transfer to the moxibustion unit 730.

Here, in the present embodiment, the protrusion member 721a is inserted into the heat radiation port 726 so that the heat accumulated in the heat storage material 721 can be more efficiently transferred to the moxibustion unit 730. However, in some cases, the heat radiation port 726 and the protrusion member 721a may be spaced apart from each other.

At this time, the partition member 725 separates the upper case 712 and the lower case 714 to improve the heat storage performance of the heat storage material 721 and minimize unnecessary heat radiation in portions other than the heat radiation port 726, thereby increasing a usage time of the moxibustion apparatus 700.

In addition, a heat insulating material is filled between the heat storage material and the partition member and between the partition member and the lower case to improve the heat storage performance, so that the heat of the heat storage material may be stored without being easily released. At this time, a variety of heat insulating materials ranging from inorganic insulating materials such as ceramic fibers to vacuum stainless-steel insulating materials can be used as the filling heat insulating material.

In addition, the heat storage material 721 may be fixed to the partition member 725 so as not to be in contact with the lower case 714, so that an increase in the temperature of the lower case 714 caused by the heat generated from the heat storage material 721 can be minimized. That is, the heat storage material 721 that generates heat may be positioned apart from the lower case 714 to prevent the lower case 714 from being heated unnecessarily.

Meanwhile, the moxibustion apparatus 700 according to the present embodiment may include the moxibustion unit 730. The moxibustion unit 730 may transfer heat to acupuncture points such as Zhongwan points of the abdomen. One side of the moxibustion unit 730 may be arranged inside the case 710 and may be directly or indirectly brought into contact with the heat storage unit 720, thereby receiving the heat accumulated in the heat storage material 721.

In addition, the other side of the moxibustion unit 730 is positioned to be exposed to the outside of the case 710, and is brought into close contact with the acupuncture points such as Zhongwan points of the abdomen, thereby locally heating the acupuncture points. At this time, an end portion of the moxibustion unit 730 which is in contact with the human body may be formed into a spherical or gently curved shape, so that the human body is not injured, and at the same time the acupuncture points can be pressed to a predetermined degree.

Here, the moxibustion unit 730 may be made of various natural stone materials such as jade, germanium, tourmaline, elvan, ceramics, gold, silver, and the like. However, any material may be used as the material of the moxibustion unit 730 as long as it can transfer heat to the acupuncture points or the like, and is not limited to the above-described materials.

The moxibustion apparatus 700 according to the present embodiment may include a heat insulating unit 740. The heat insulating unit 740 may be positioned between the heat storage material 721 and the moxibustion unit 730 so that the heat accumulated in the heat storage material 721 can be selectively directed to the moxibustion unit 730.

Figure 9:
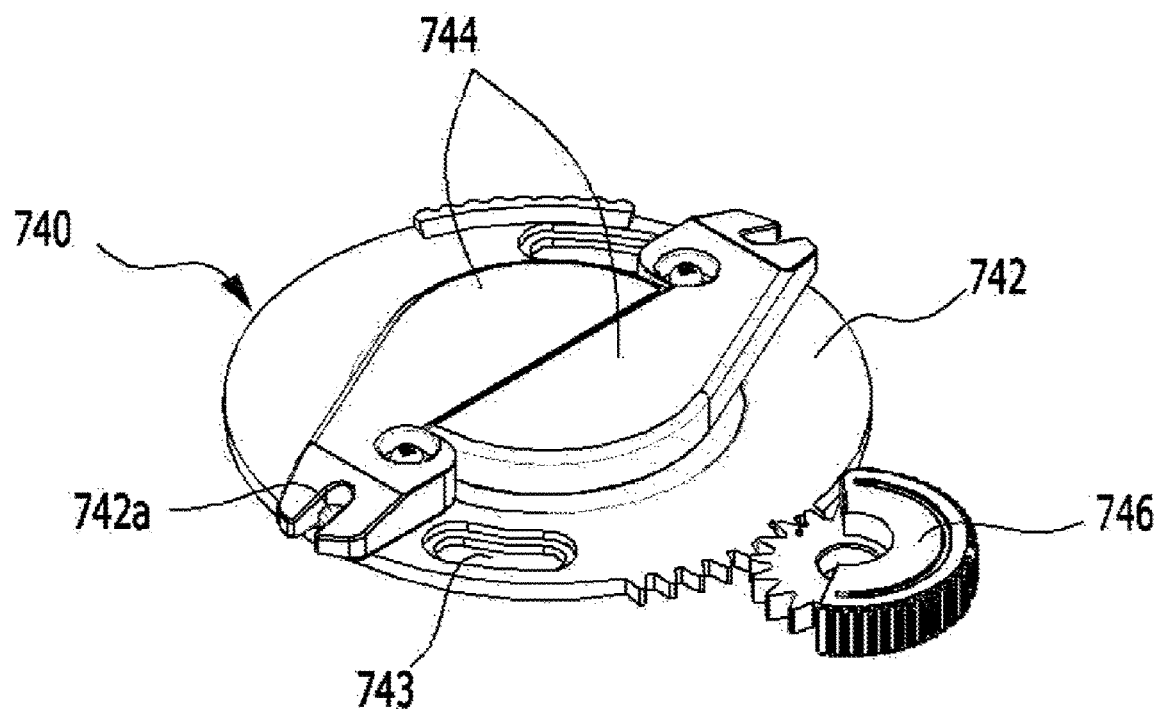
FIG. 9 is a diagram schematically showing a heat insulating unit in the moxibustion apparatus shown in FIG. 5.
Figure 9:
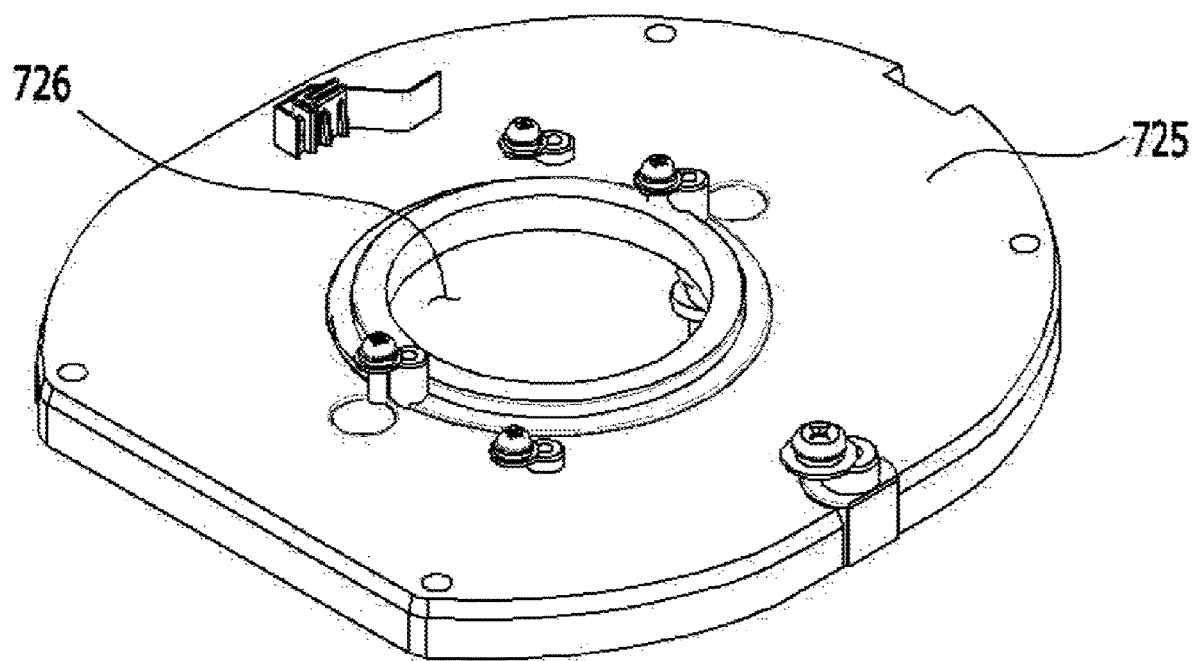

Specifically, as shown in FIG. 9, the heat insulating unit 740 may be positioned between the partition member 725 and the moxibustion unit 730. The heat insulating unit 740 may include a rotary member 742 formed with a hollow at the same position as the heat radiation port 726 formed in the partition member 725, a heat insulating member 744 capable of selectively opening or blocking the hollow, and an adjusting member 746 that rotates the rotary member 742 to provide a driving force so that the heat insulating member 744 can be operated.

The rotary member 742 is rotatably installed with respect to the partition member 725 to transmit a driving force to the heat insulating member 744 to be described later, and is coupled to the partition member 725 through a screw. At this time, the rotary member 742 is formed in a ring shape, and a long hole 743 is formed in a portion where the screw is engaged so that the operation range of an adjusting member is controlled and the rotary member 742 is rotatably arranged.

Figure 10A:
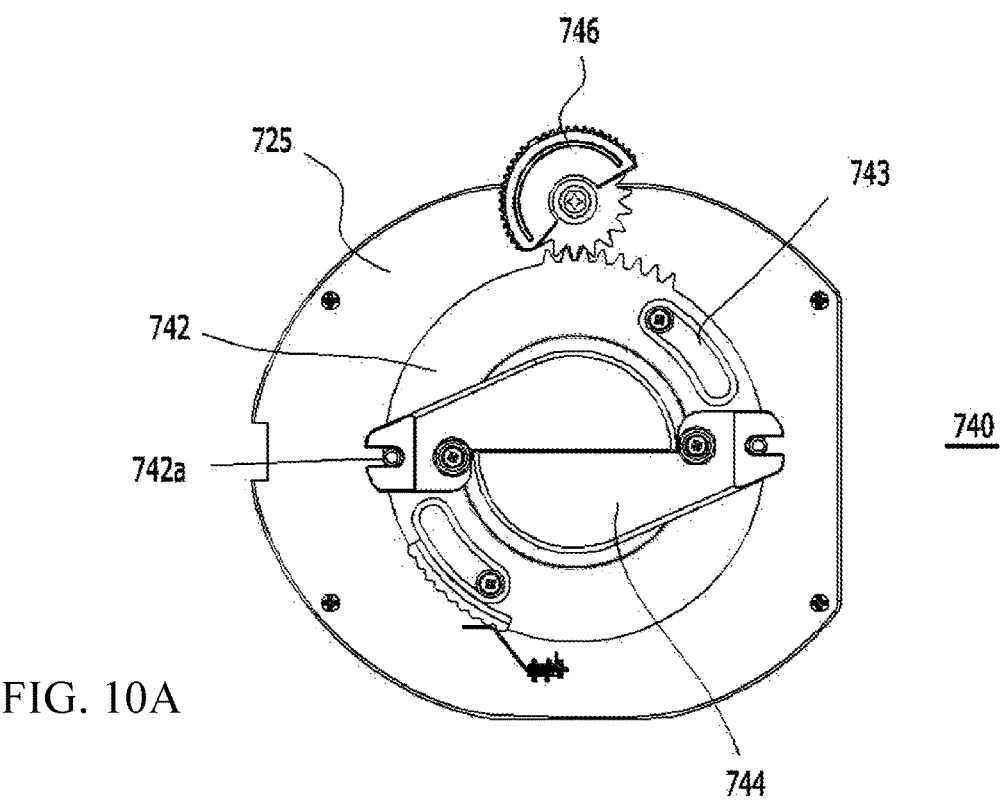
FIGS. 10A and 10B are views showing a combined state and an operational state of FIG. 9.
Figure 10B:
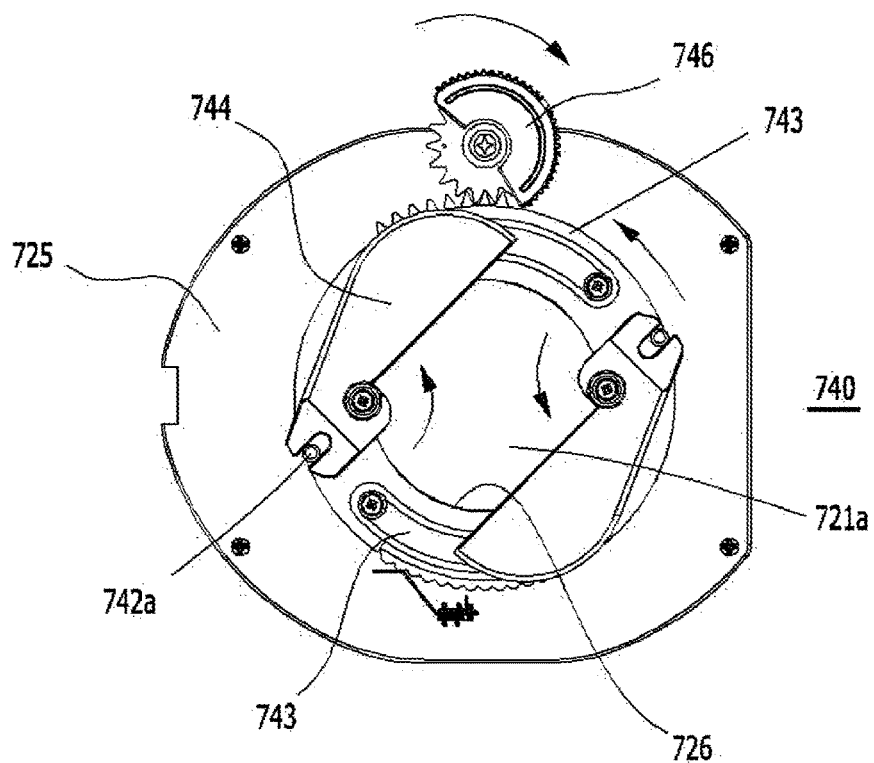

As shown in FIGS. 10A and 10B, in a structure in which one end of the heat insulating member 744 is rotatably arranged on a fixing pin 742a formed so as to protrude from the rotary member 742 and a portion adjacent to a portion that is rotatably and slidably coupled to the fixing pin 742a is hinge-coupled to the partition member 725, the protrusion member 721a of the heat storage material 721 positioned in the heat radiation port 726 may be selectively sealed, so that the heat generated from the heat storage material 721 can be prevented from being transmitted to the moxibustion unit 730 to a predetermined degree (FIG. 10A is a view showing a state in which the heat radiation port 726 is blocked and FIG. 10B is a view showing a state in which the heat insulating member 744 is rotated to open the heat radiation port so that the heat transfer is allowed).

Here, the heat insulating member 744 is made of a material having low thermal conductivity, and may be made of any material as long as it can reduce the transfer of heat generated from the heat storage material 721 to the moxibustion unit 730.

Accordingly, an amount of heat radiation from the heat storage material 721 to the moxibustion unit 730 can be reduced by the action of the heat insulating member 744, and the temperature of the moxibustion unit 730 can be lowered by a predetermined degree.

Meanwhile, the heat insulating unit 740 may further include the adjusting member 746.

The adjusting member 746 rotates the rotary member 742 so that the heat insulating member 744 can be operated. One side of the adjusting member 746 is exposed to the outside of the case 710 so that a user can rotate the adjusting member 746 by a predetermined degree as needed. The other side of the adjusting member 746 is positioned inside the case 710 and is engaged with the rotary member 742 in a gear-like manner. That is, a toothed wheel-shaped first gear is formed at a rim of the rotary member 742, and a second gear is formed at the adjusting member 746 so as to be engaged with the first gear.

Accordingly, when a user rotates the adjusting member 746, the gear-engaged rotary member 742 is rotated in a direction of an arrow shown in the drawing, and as the rotary member 742 is rotated, the heat insulating member 744 may open or close the heat radiation port 726. At this time, the user can appropriately adjust a degree of opening of the heat radiation port 726 according to the usage, taste, etc., when the moxibustion apparatus 700 is used, thereby adjusting the temperature of the moxibustion unit 730.

Figure 11:
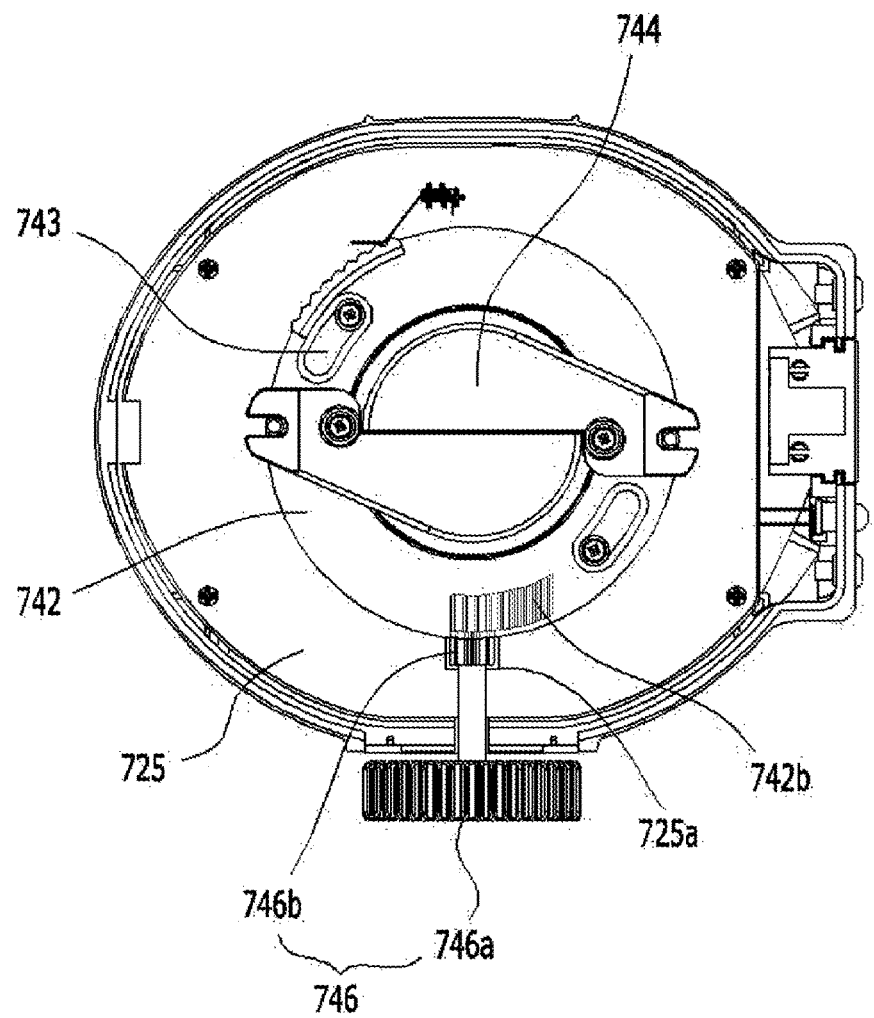
FIG. 11 is a view showing another embodiment of an adjusting member in the moxibustion apparatus shown in FIG. 5.
Figure 11:
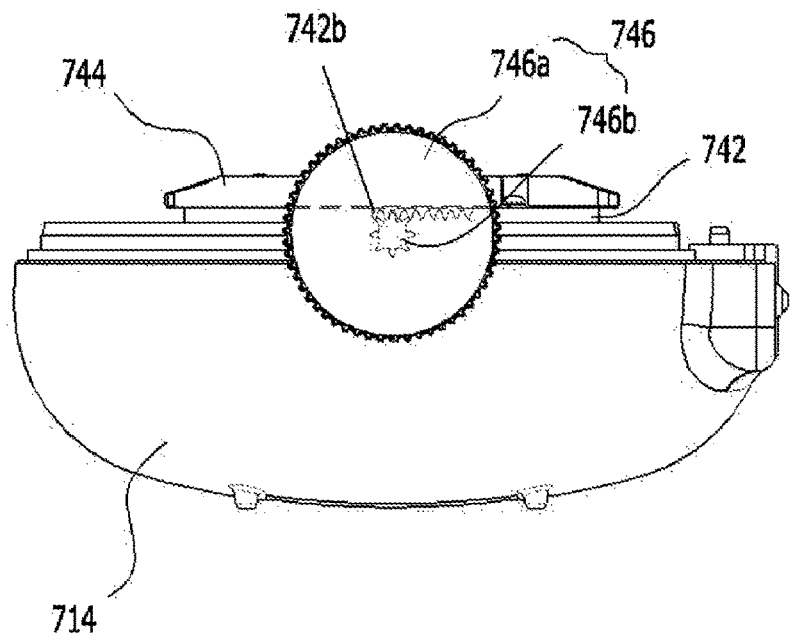

FIG. 11 is a view showing another embodiment of an adjusting member 746 in the moxibustion apparatus 700 shown in FIG. 5.

Referring to FIG. 11, one end of the adjusting member 746 according to the present embodiment may be exposed to the outside and the other end thereof may be in contact with a front surface or a rear surface of the rotary member 742. At this time, a rack gear 742b may be formed on the front surface when the adjusting member 746 is in contact with the front surface of the rotary member 742, and may be formed on the rear surface when the adjusting member 746 is in contact with the rear surface of the rotary member 742.

In the present embodiment, a case in which the other end of the adjusting member 746 is in contact with the rear surface of the rotary member 742 is described.

Referring to this, the one end of the adjusting member 746, that is, a lever portion 746a which a user can rotate, is positioned so as to be completely exposed to the outside of the case 710, and the other end thereof is formed with a toothed wheel portion 746b so as to be engaged with the rack gear 742b famed on the rear surface of the rotary member 742.

At this time, the toothed wheel portion 746b of the adjusting member 746 that is engaged with the rack gear 742b is positioned in a rotation hole 725a formed such that a part of the partition member 725 is perforated, so that the toothed wheel portion 746b may be stably rotated. Accordingly, the adjusting member 746 according to the present embodiment adjusts a degree of opening/closing of the heat insulating member 744 in such a manner that the adjusting member 746 may be adjusted by a user in a state of being completely exposed to the outside of the case 710. This is different from the adjusting member 746 of the above-described embodiment.

Figure 12:
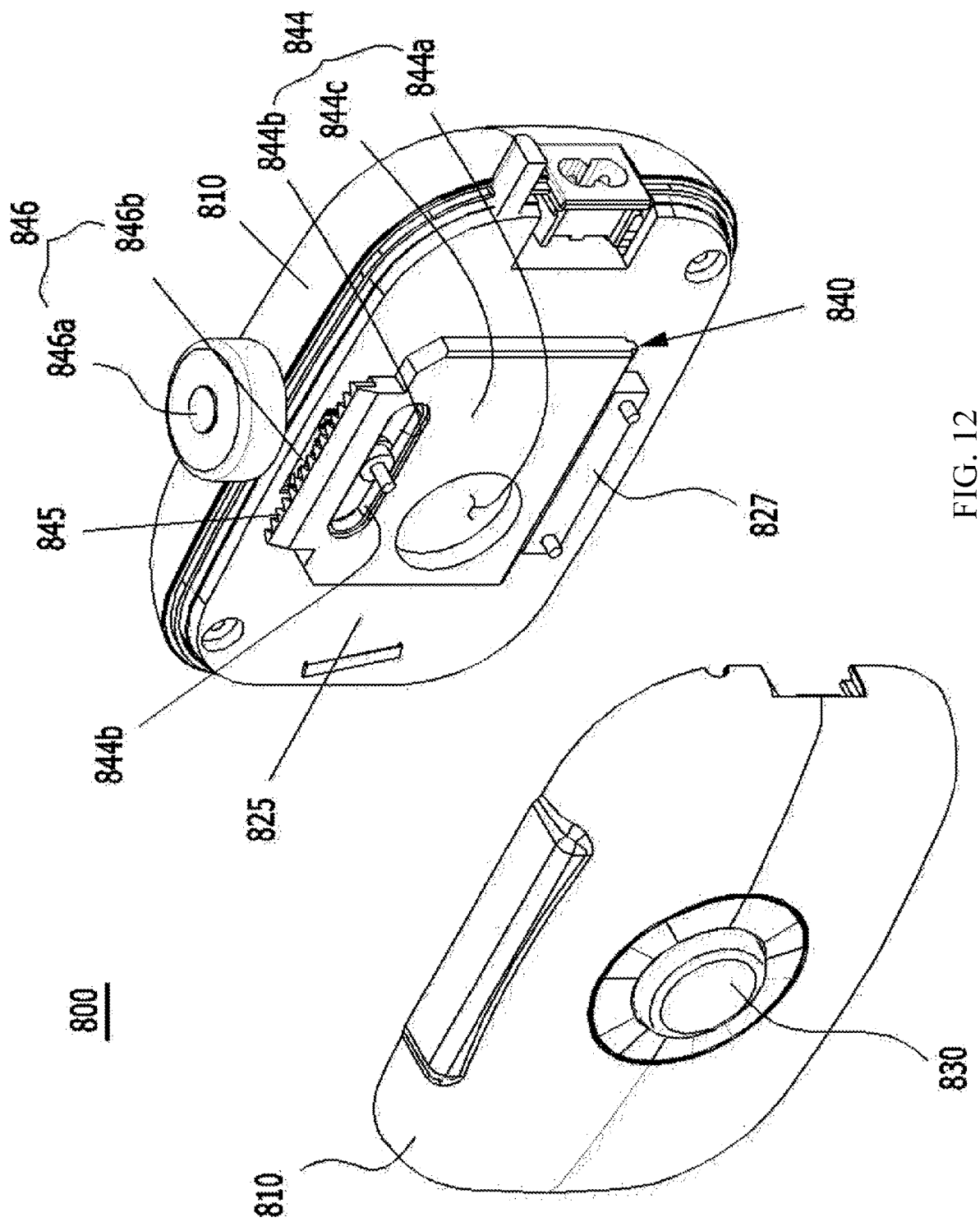
FIG. 12 is an exploded perspective diagram schematically showing a moxibustion apparatus according to a fourth embodiment of the present invention.
Figure 13:
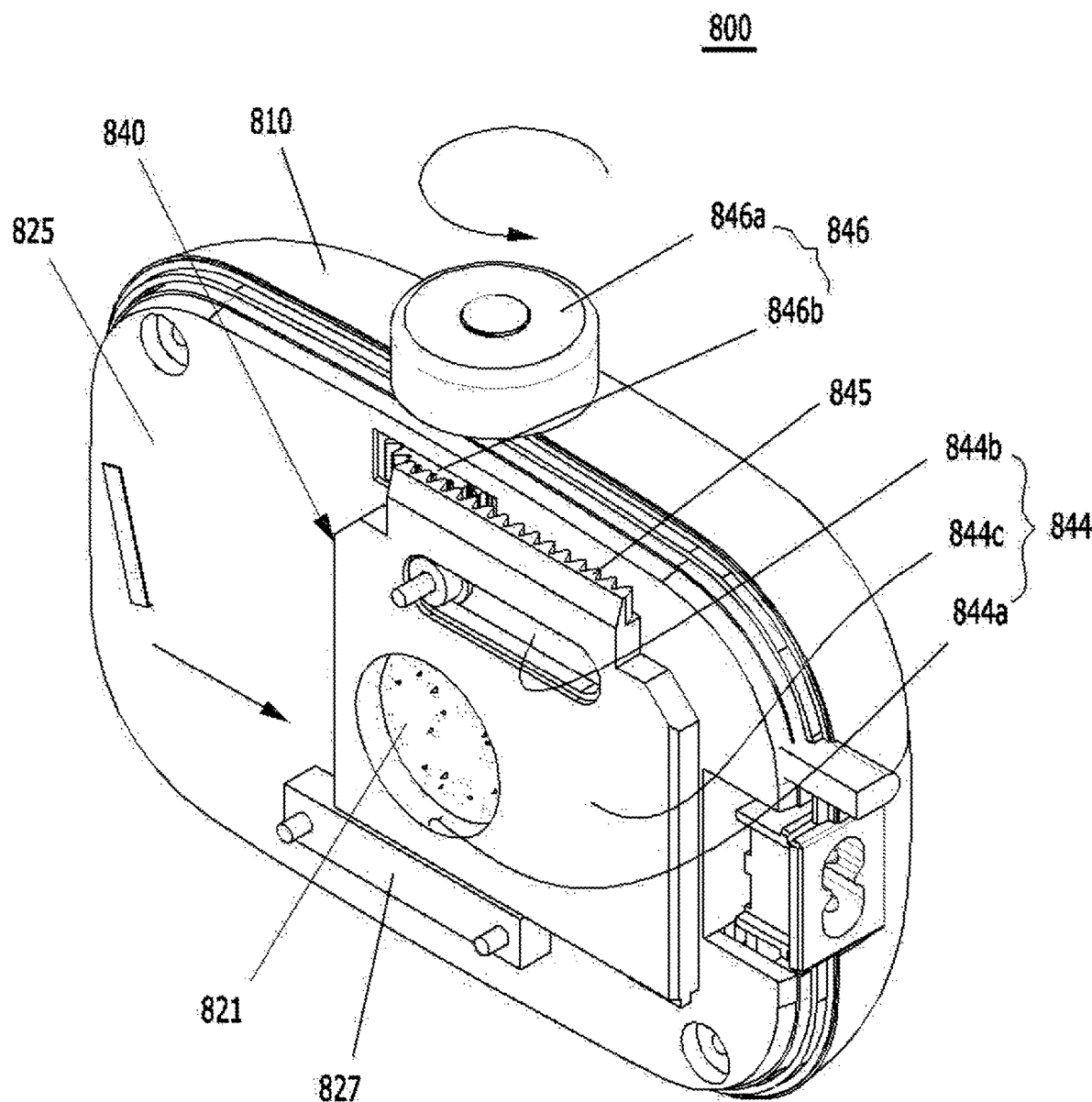
FIG. 13 is a diagram schematically showing an operating state of the moxibustion apparatus shown in FIG. 12.

FIG. 12 is an exploded perspective diagram schematically showing a moxibustion apparatus 800 according to a fourth embodiment of the present invention, and FIG. 13 is a diagram schematically showing an operating state of the moxibustion apparatus 800 shown in FIG. 12.

Referring to FIGS. 12 and 13, similar to the above-described embodiment, the moxibustion apparatus 800 according to the present embodiment may include a case 810, a heat storage unit (not shown) provided inside the case 810 to generate heat, a moxibustion unit 830 that receives the heat provided from the heat storage unit to heat a human body, and a heat insulating unit 840 that blocks or allows transfer of the heat provided from the heat storage unit.

However, there is a difference in the structure of the heat insulating unit 840 in this embodiment. Therefore, in the case of this embodiment, detailed description of the case 810, the heat storage unit, and the moxibustion unit 830 will be omitted, and only the structure of the heat insulating unit 840 having a difference with the above-described embodiment will be described in detail.

As shown in FIGS. 12 and 13, the heat insulating unit 840 of the moxibustion apparatus 800 according to the present embodiment may include a heat insulating member 844 that covers, in a sliding manner, a heat storage material 821 positioned in a heat radiation port (not shown) formed in a partition member 825, and an adjusting member 846 that allows the heat insulating member 844 to slide.

Specifically, the heat insulating member 844 is formed in a plate shape and is formed to have an opening portion 844a at a part thereof, and is slidably engaged with the partition member 825. That is, the heat insulating member 844 is screwed to the partition member 825, and a long hole 844b is formed in a portion of the heat insulating member 844 screwed to the partition member 825, so that the heat insulating member 844 may be movable in position.

At this time, the heat insulating member 844 includes the opening portion 844a through which the heat provided from the heat storage material 821 can be transferred to the moxibustion unit 830, and a blocking portion 844c that is formed to seal the heat radiation port (not shown) to minimize heat transfer, so that the heat radiated from the heat storage material 821 can be prevented from being transferred to the moxibustion unit 830 due to the positional movement of the heat insulating member 844.

In addition, in the present embodiment, the moxibustion apparatus 800 may further include a guide member 827 that is formed at one side of the partition member 825 and guides the sliding of the heat insulating member 844. The guide member 827 guides the heat insulating member 844 when the heat insulating member 844 slides, so that heat insulating member 844 can be moved smoothly.

Meanwhile, the adjusting member 846 includes a lever portion 846a that is positioned outside the case 810, and an engagement portion 846b that extends from the lever portion 846a and is engaged with a rack gear 845 famed in the heat insulating member 844.

The engagement portion 846b may be engaged with the rack gear 845 formed on a front surface or a rear surface of the heat insulating member 844, so that the position of the heat insulating member 844 can be varied in a sliding manner when a user rotates the lever portion 846a.

As described above, the moxibustion apparatus according to the embodiments of the present invention may perform moxibustion on acupuncture points or Zhongwan points of the abdomen by heating a heat storage unit through an external power source for a predetermined time period and then radiating the heat accumulated in the heat storage unit through a moxibustion unit. In particular, the moxibustion apparatus according to the embodiments of the present invention may be very easily carried and convenient for regular use even during outdoor activities and everyday life by performing a moxibustion function through the accumulated heat after a certain time period of charge (heat storage). This can be contrasted with the inconvenience of moxibustion in everyday life and outdoor activities because a conventional moxibustion technique locally heats acupuncture points or the like by burning medicinal substances.

Meanwhile, the moxibustion apparatus according to the embodiments of the present invention may be used for locally heating the acupuncture points or Zhongwan points of the abdomen. Here, a heat storage material is entirely surrounded by a heat insulating member to minimize unnecessary heat radiation, and heat transfer and heat radiation is achieved only through an exposed portion. Therefore, the usage time of the moxibustion apparatus according to the embodiments of the present invention can be greatly increased as compared with the conventional moxibustion apparatus in which heat is radiated through the entire outer surface thereof. In addition, since heat radiation is performed in a state in which the protruding moxibustion unit is embedded in the abdomen portion by a predetermined amount due to the pressing of a belt or the like, sufficient heat radiation is possible even in a minimum amount of heat radiation.

In addition, in the moxibustion apparatus according to the embodiments of the present invention, a heat storage unit in which heat is accumulated and a moxibustion unit that heats a human body can be separately formed so that a heat storage material can be made of a relatively inexpensive material, and the moxibustion unit having the a relatively small volume can be made of expensive materials that have various beneficial effects such as anion and far-infrared emission, and the like. Therefore, it is possible to use a heat storage material formed of an inexpensive material while enjoying various beneficial effects due to expensive materials, thereby minimizing an increase in manufacturing cost.

Further, the moxibustion apparatus according to the embodiments of the present invention can be easily worn by a belt or the like, so that it can be continuously used even when a user is engaged in external activities or everyday life. In addition, the moxibustion apparatus according to the embodiments of the present invention is rechargeable, so that there is no fear of being affected by electromagnetic waves even when it is used for a long time period. In addition, in the conventional moxibustion method, smell, ashes, and the like are generated and the temperature thereof cannot be adjusted, whereas the moxibustion apparatus according to the embodiments of the present invention generates no smell, ashes, etc., and the temperature thereof can be easily adjusted through a heat radiation amount adjusting unit.

While the embodiments of the present invention have been described, it will be apparent to those skilled in the art that additions, alterations, deletions, or additions of components may be made without departing from the scope of the present invention as set forth in the claims. It will be understood that various modifications and changes may be made by those skilled in the art without departing from the scope of the present invention.

What is claimed is:

1. A moxibustion apparatus comprising:
   a case including a front case, a rear case, and an inner case, wherein the front case and the rear case form an outer surface of the moxibustion apparatus, and the inner case is disposed in the case and includes a heat radiation port;
   a heat storage unit configured to be arranged inside the case and including a heat storage material and a heat insulating member that covers an outer surface of the heat storage material, wherein an exposed portion of the heat storage material is exposed to outside of the heat insulating member and is arranged to correspond to the heat radiation port;
   a moxibustion unit configured to receive heat accumulated in the heat storage material through the exposed portion to locally heat acupuncture points of a user's abdomen, and to have one side thereof exposed to outside of the case; and
   a heat radiation amount adjusting unit arranged between the exposed portion and the moxibustion unit and configured to adjust an amount of heat transferred through the heat radiation port by adjusting a thermal resistance between the exposed portion and the moxibustion unit.

2. The moxibustion apparatus of claim 1, wherein the heat radiation amount adjusting unit is fastened to the inner case to be movable relative to the heat radiation port to a predetermined degree, and includes a heat insulating block and a heat transfer block arranged to be spaced apart from each other by a predetermined distance with the heat radiation port interposed therebetween and a lever portion exposed to the outside of the case.

3. The moxibustion apparatus of claim 1, wherein the heat radiation amount adjusting unit adjusts the thermal resistance between the exposed portion and the moxibustion unit by placing one of a plurality of elements that have respective thermal conductivities in a space between the exposed portion and the moxibustion unit.

4. A moxibustion apparatus comprising:
   a case;
   a heat storage unit configured to be provided inside the case to accumulate heat by power supplied from an external power source, and to radiate the accumulated heat through a heat radiation port;
   a moxibustion unit configured to receive the heat radiated from the heat storage unit to heat a human body; and
   a heat insulating unit including a hollow at the same position as the heat radiation port and configured to block or allow transfer of the heat provided from the heat storage unit by selectively opening or closing the hollow.

5. The moxibustion apparatus of claim 4, wherein the heat storage unit includes:
   a heat storage material configured to allow heat required for moxibustion to be accumulated;
   a heating member configured to be embedded in the heat storage material and be electrically heated to allow heat to be accumulated in the heat storage material; and
   a partition member configured to divide the case to restrict the heat radiated to the heat storage material from being transferred to the moxibustion unit, and to have the heat radiation port formed at a portion thereof.

6. The moxibustion apparatus of claim 5, wherein the heat insulating unit includes:
   a rotary member configured to be rotatably positioned between the heat storage unit and the moxibustion unit, and to have the hollow at the same position as the heat radiation port formed in the partition member of the heat storage unit;
   a heat insulating member configured to be formed to selectively open and close the hollow, to be rotatably coupled to the rotary member in an end thereof, and to be hinge-coupled to the partition member of the heat storage unit in a position thereof adjacent to a portion in which the heat insulating member is rotatably coupled to the rotary member; and
   an adjusting member configured to rotate the rotary member so that the heat insulating member is rotated, and to allow or block transfer of the heat provided from the heat storage unit to the moxibustion unit.

7. The moxibustion apparatus of claim 6, wherein one side of the adjusting member is exposed to the outside of the case so that a user rotates the adjusting member to a predetermined degree as needed, and the other side thereof is positioned inside the case so that the adjusting member is engaged with the rotary member in a toothed wheel shape.

8. The moxibustion apparatus of claim 4, wherein the heat insulating unit includes:
   a heat insulating member configured to cover or open the heat radiation port formed in the partition member of the heat storage unit in a sliding manner; and
   an adjusting member configured to allow the heat insulating member to slide.

9. The moxibustion apparatus of claim 4, wherein the heat insulating unit includes:
   a rotary member configured to be rotatably positioned between the heat storage unit and the moxibustion unit, and having the hollow at the same position as the heat radiation port; and
   a heat insulating member configured to selectively open or close the hollow and being rotatably coupled to the rotary member.

* * * * *